United States Patent
Liu et al.

(10) Patent No.: US 6,926,815 B2
(45) Date of Patent: Aug. 9, 2005

(54) COPOLYMERS FOR CAPILLARY GEL ELECTROPHORESIS

(75) Inventors: Changsheng Liu, State College, PA (US); Qingbo Li, State College, PA (US)

(73) Assignee: SpectruMedix LLC, State College, PA (US)

( * ) Notice: Subject to any disclaimer, the term of this patent is extended or adjusted under 35 U.S.C. 154(b) by 780 days.

(21) Appl. No.: 09/843,918

(22) Filed: Apr. 30, 2001

(65) Prior Publication Data

US 2001/0023827 A1 Sep. 27, 2001

Related U.S. Application Data

(63) Continuation of application No. PCT/US00/00793, filed on Jan. 12, 2000.
(60) Provisional application No. 60/115,588, filed on Jan. 12, 1999.

(51) Int. Cl.[7] ...................... G01N 27/441; G01N 27/453
(52) U.S. Cl. ........................................ 204/455; 204/605
(58) Field of Search .............................. 204/451, 455, 204/469, 601, 605

(56) References Cited

U.S. PATENT DOCUMENTS

| | | | |
|---|---|---|---|
| 4,048,377 A | 9/1977 | Boschetti et al. | 428/474.4 |
| 4,254,249 A * | 3/1981 | Cottrell et al. | 525/329.4 |
| 4,725,343 A | 2/1988 | Hjerten et al. | 204/548 |
| 4,844,786 A | 7/1989 | Sugihara et al. | 204/616 |
| 4,874,490 A | 10/1989 | Hochstrasser | 204/467 |
| 4,877,510 A | 10/1989 | Chen | 204/613 |
| 4,948,480 A | 8/1990 | Christy, Jr. et al. | 204/470 |
| 4,963,243 A | 10/1990 | Ogawa et al. | 204/469 |
| 4,997,537 A | 3/1991 | Karger et al. | 204/453 |
| 5,006,210 A | 4/1991 | Yueng et al. | 204/452 |
| 5,055,517 A | 10/1991 | Shorr et al. | 524/813 |
| 5,069,766 A | 12/1991 | Zhu et al. | 204/454 |
| 5,149,416 A | 9/1992 | Osterhoudt et al. | 204/456 |
| 5,164,055 A | 11/1992 | Dubrow | 204/455 |
| 5,545,302 A | 8/1996 | Zhu et al. | 204/454 |
| 5,552,028 A | 9/1996 | Madabhushi et al. | 204/451 |
| 5,567,292 A | 10/1996 | Madabhushi et al. | 204/451 |
| 5,569,364 A | 10/1996 | Hooper et al. | 204/455 |

(Continued)

FOREIGN PATENT DOCUMENTS

| | | |
|---|---|---|
| EP | 0 324 539 A2 | 1/1989 |
| EP | 0 339 678 A2 | 4/1989 |
| EP | 0 340 653 A2 | 4/1989 |

OTHER PUBLICATIONS

Hirokazu Sawada & Kiyokatsu Jinno "Capillary electrophoretic separation of structurally similar solutes in non-cross-linked poly(acrylamide-co-isopropylacrylamide solutin" Electrophoresis (1997) vol. 18, pp. 2030–2035.*

(Continued)

*Primary Examiner*—Alex Noguerola
(74) *Attorney, Agent, or Firm*—Fish & Richardson P.C.

(57) ABSTRACT

This invention relates to an electrophoresis separation medium having a gel matrix of at least one random, linear copolymer comprising a primary comonomer and at least one secondary comonomer, wherein the comonomers are randomly distributed along the copolymer chain. The primary comonomer is an acrylamide or an acrylamide derivative that provides the primary physical, chemical, and sieving properties of the gel matrix. The at least one secondary comonomer imparts an inherent physical, chemical, or sieving property to the copolymer chain. The primary and secondary comonomers are present in a ratio sufficient to induce desired properties that optimize electrophoresis performance. The invention also relates to a method of separating a mixture of biological molecules using this gel matrix, a method of preparing the novel electrophoresis separation medium, and a capillary tube filled with the electrophoresis separation medium.

22 Claims, 3 Drawing Sheets

U.S. PATENT DOCUMENTS

| | | | |
|---|---|---|---|
| 5,728,282 A | | 3/1998 | Bashkin et al. ............. 204/455 |
| 5,759,369 A | | 6/1998 | Menchen et al. ........... 204/456 |
| 5,785,832 A | | 7/1998 | Chiari et al. ................ 204/469 |
| 5,885,432 A | | 3/1999 | Hooper et al. .............. 204/469 |
| 6,013,359 A | * | 1/2000 | Takano et al. .............. 428/219 |
| 6,117,293 A | | 9/2000 | Zhang et al. |
| 6,464,850 B1 | * | 10/2002 | Zhang et al. ................ 204/455 |

OTHER PUBLICATIONS

Hirokazu Sawada & Kiyokatsu Jinno "Capillary electrophoresis with linear polymers containing Hydrophobic groups for the separation of small molecules" Analyst (1998), vol. 123, pp. 1471–1476.*

*Separation of polyelectrolytes of variable compositions by free–zone capillary electrophoresis; Journal of Chromatography A*, 766 (1997) pp. 233–236.

*Separations of DNA fragments by capillary electrophoresis in N–substituted polyacrylamides; Journal of Chromatography A*, 781 (1977) pp. 347–355.

*Multiplexed Fluorescence Detector for Capillary Electrophoresis Using Axial Optical Fiber Illumination; Analytical Chemistry*, vol. 65 No. 7, Apr. 1, 1993 pp. 958–960.

*Simultaneous Monitoring of DNA Fragments Separated by Electrophoresis in a Multiplexed Array of 100 Capillaries; Analytical Chemistry*, vol. 66 No. 9, May 1, 1994; pp. 1424–1431.

*High Speed DNA Sequencing by Using Mixed Poly(ethylene oxid) Solutions in Uncoated Capillary Columns; Analytical Chemistry*, vol. 6 No. 13, Jul. 1, 1995; pp. 1913–1919.

* cited by examiner

COPOLYMERS FOR CAPILLARY GEL ELECTROPHORESIS

RELATED APPLICATIONS

The present application is a Continuation of International Application No. PCT/US00/00793 filed Jan. 12, 2000, which itself claims priority to U.S. Provisional Patent Application No. 60/115,588, filed Jan. 12, 1999.

TECHNICAL FIELD

This invention relates to an electrophoresis separation medium that can be flexibly optimized by combining multiple required features into one polymeric gel matrix via random copolymerization of selected multiple monomers.

BACKGROUND OF THE INVENTION

The movement of a molecule with a net charge in an electric field is known as electrophoresis. Electrophoresis is a powerful means of separating biological molecules such as proteins, peptides, oligonucleotides, RNA and DNA. The velocity of migration (v) of a molecule in an electric field depends on the electric field strength (E), the net charge of the protein (z), and the frictional coefficient (f), as shown in the equation:

$$v = \frac{Ez}{f}$$

Two primary separating mechanisms exist: (i) separations based on differences in the effective charge of the analytes, and (ii) separations based on molecular size. Separations based on differences in the effective charge are usually limited to low or moderate molecular weight molecules since high molecular weight molecules have effective charges that are similar, making it difficult to separate them. Separations based on molecular size are generally referred to as molecular sieving and are conducted using gel matrices that have controlled pore sizes. In these separating systems, if the effective charges of the analytes are the same, the separation results from differences in the abilities of the different sized molecular species to penetrate through the gel matrix. Smaller molecules move more quickly relative to larger ones through a gel of a given pore size.

In theory, separation of different proteins could be achieved readily in free solution provided that the molecules differed sufficiently in their charge densities. In practice, separations in free solutions are difficult to achieve because the heat produced during electrophoresis can cause convection disturbances which distort the protein bands. As a result, band broadening occurs and protein resolution is compromised. For this reason, electrophoresis in free solution is rarely practiced.

Various support media are used to minimize convection and diffusion, such as paper or cellulose acetate, agarose, starch and polyacrylamide. Paper, cellulose acetate, and similar porous materials are relatively inert, serve mainly for support and to minimize convection, and separation of proteins is based largely on the charge density of the proteins at a specific pH.

Starch, agarose and polyacrylamide gels are the preferred media for conducting electrophoretic separations. These gels not only minimize convection and diffusion, but also actively participate in the separation process. More specifically, these materials provide a restrictive medium where molecular sieving occurs, and provides separation on the basis of both charge density and molecular size. Polyacrylamide-based gels are widely used because they are chemically inert, have excellent sieving characteristics, and have high resolution capabilities. However, polyacrylamide-based gels have high viscosity, may form air bubbles that affect separation, have a short shelf life, are neurotoxic, and are cumbersome to prepare.

Electrophoresis may be carried out using slab gels, which typically run several samples in parallel lanes. Large samples of DNA are required, and detection of the DNA typically occurs after the electrophoretic separation is complete. Advantages of this technique include the ease of post-separation sample collection, the ability to compare results of multiple samples on the same gel, and the ability to separate large amounts of DNA. However, slab gel electrophoresis can be labor-intensive and slow.

Alternatively, capillary electrophoresis (CE) permits rapid, high resolution separation of molecules. CE typically involves the separation of charged molecules in a narrow capillary with on-line detection by either absorbance or laser-induced fluorescence. Typically, CE employs fused silica capillary tubes whose inner diameters are between 50 microns to 200 microns, and have lengths ranging from 10 cm to 100 cm or more. These capillaries can be coated, typically with polyacrylamide, or left uncoated. The coating prevents electroendoosmotic flow, a phenomenon which frequently occurs in electrophoretic separations of solute ions dissolved in a solvent or solvent system. This phenomenon causes bulk flow of the solvent system in response to the applied electric field. The bulk flow impairs the separation of solutes since it causes mobilization of all solutes at a common rate as part of the solution in which they are dissolved. This effectively shortens the path of travel attributable to electrophoresis, and thereby lessens the degree of electrophoretic separation for a column of a given length.

Crosslinked polymers, such as polyacrylamide and other high viscosity media, are not suitable for CE since the high viscosity makes replacement of the gel in the capillary an impractical matter. Separation also takes a longer period of time using crosslinked polymers when compared to low viscosity media.

Linear polyacrylamide ("LPA") is a highly effective separation medium that has excellent sieving properties due to its entanglement structure. Furthermore, the absence of crosslinking in a linear polymer gives it lower viscosity. In order to use LPA in CE, the capillary inner wall must be coated with a hydrophilic polymer to suppress electroendoosmotic flow in order to achieve expected separation performance. Coating the inner surface of capillary walls to prevent electroendoosmosis is known. For example, U.S. Pat. No. 5,545,302 discloses the suppression of electroendoosmotic flow in CE by the use of amine-derivatized polymers. U.S. Pat. No. 5,552,028 discloses the suppression of electroendoosmostic flow in CE by the use of N,N'-disubstituted or N-monosubstituted polyacrylamides, which have self-coating properties. These amine-derivatized polymers were prepared by modifying the functional groups of a pre-existing homopolymer to impart the desired self-coating characteristic. U.S. Pat. No. 4,997,537 discloses a silane-derivatized coating covalently bonded to the inner surface of a microcapillary wall, a thin layer of a hydrophilic polymer absorbed on the layer of the coating material, and a polyacrylamide gel filling the tube.

Other polymers, such as poly(ethylene oxide), poly(dimethylacrylamide) (U.S. Pat. Nos. 5,567,292 and 5,552,028), and poly(vinylpyrrolidone) (Gao et al., Analytical Chem., 1998, 70, 1383–1388) are able to suppress electroendoosmotic flow during DNA separation in uncoated capillaries. However, none of these polymers has been shown to surpass the performance of linear polyacrylamide in the aspects of DNA sequencing read length and capability of high speed separation at elevated temperature.

The use acrylamide derivatives to synthesize polymeric gel matrices is known (Sassi et al., Electrophoresis, 1996, 17, 1460; U.S. Pat. No. 5,470,916; and Lindberg et al. Electrophoresis, 1997, 18, 2909). Gel Matrices synthesized from these acrylamide derivatives usually have significant physical, chemical, and electrophoretic properties from polyacrylamide.

The use of copolymers in electrophoresis media to enhance performance are known. For example, U.S. Pat. No. 4,997,537 discloses the use of a copolymer of polyacrylamide and a crosslinker, such as N,N'-methylenebisacrylamide, in microcapillary gel electrophoresis. U.S. Pat. Nos. 4,948,480 and 5,149,416 disclose gel electrophoresis media composed of a water-soluble copolymer of an acrylamide monomer with another comonomer that facilitates crosslinking via a crosslinking agent. U.S. Pat. No. 5,759,369 discloses an electrophoresis separation medium composed of a copolymer containing a linear hydrophilic polymer segment having uniform segment length and hydrophobic polymer segments at each end. These copolymers may have one of the following structures: i) comb or tuft copolymer structure; ii) block copolymer structure; and iii) star copolymer structure, but none are random copolymers. Liang et al. (Electrophoresis, 1998, 19, 2447–2453) discuss capillary electrophoresis using a non-crosslinked triblock polymer.

Despite the great amount of effort which has gone into improving conventional electrophoresis separation media, there is a need for new polymeric media that incorporate specific properties to overcome general problems associated with electrophoretic separations, and to enhance electrophoresis separation performance in various applications. What is also desirable is an electrophoresis gel medium for coated and uncoated capillaries that is capable of resolving DNA fragments comprising 500 to 1000 base pairs.

SUMMARY OF THE INVENTION

This invention relates to an electrophoresis separation medium having a gel matrix of at least one random, linear copolymer comprising a primary comonomer and at least one secondary comonomer, wherein the comonomers are randomly distributed along the copolymer chain. The primary comonomer is an acrylamide or an acrylamide derivative that provides the primary physical, chemical, and sieving properties of the gel matrix. The at least one secondary comonomer imparts an inherent physical, chemical, or sieving property to the copolymer chain, and primary and secondary comonomers are present in a ratio sufficient to induce desired properties that optimize electrophoresis performance.

The desired properties incorporated by the secondary comonomers are hydrophilicity, hydrophobicity, copolymer chain backbone stiffness, stability of copolymer entanglement structure, resistance to hydrolysis, processivity of copolymer chain extension, gel matrix viscosity, affinity of the copolymer to the surface of a supporting substrate, chirality, or a mixture thereof.

Preferably, the ratio of reactivity of the at least one secondary to primary comonomer is between about 0.3 to about 2. The gel matrix generally has a viscosity of between about 1500 to about 20,000 Cp, and the linear random copolymers have molecular weights of between about 100,000 to 5,000,000 Daltons.

The present invention also relates to a method of preparing an electrophoresis separation medium containing a gel matrix of at least one random, linear copolymer comprising contacting a primary and at least one secondary comonomer in the presence of a copolymerization initiator in an aqueous medium having a pH of between about 5 to about 11 at a temperature and time sufficient to copolymerize the comonomers and form a linear, random copolymer. Contacting the random, linear copolymer in a buffer forms the gel matrix.

The present invention also relates to a capillary tube filled with the electrophoresis separation medium described herein, and to a method of separating a mixture of biological molecules by placing into a support the electrophoresis separation medium described herein, adding the mixture of biological molecules to the electrophoretic separation medium at one end of the support; and applying an electric field to the medium having a strength sufficient to facilitate the migration and separation of the biological molecules.

DETAILED DESCRIPTION OF THE INVENTION

This invention relates to gel matrices for use as electrophoresis separation media. These gel matrices contain random copolymers that may be synthesized to have desired properties to further optimize electrophoresis performance. The prior art does not teach the use of random copolymers as sieving components for gel electrophoresis media. Furthermore, the prior art does not teach the use of gel electrophoresis media containing random copolymers that can be strategically synthesized to fine tune its physical, chemical, and sieving properties.

The term "monomer" as used herein is defined as a molecule or compound usually containing carbon, of relatively low molecular weight, and simple structure that is capable of conversion to polymers by combination with itself or other similar molecules or compounds.

The term "polymer" as used herein is defined as a macromolecule formed by the chemical union of two or more identical monomers.

The term "copolymer" as used herein is defined as a polymer that is made up of more than one dissimilar monomers.

The expression "random copolymer" as used herein is defined as a copolymer that is made up of more than one monomer, in which different monomer units are distributed along a copolymer chain in no specific pattern. Unless stated otherwise, the term "copolymer" refers to random copolymers.

The expression "linear copolymer" as used herein is defined as copolymers that are not crosslinked.

The expression "random, linear copolymer" as used herein is defined as a copolymer that is made up of more than one monomer, in which different monomer units are distributed along a copolymer chain in no specific pattern, and the copolymer is not crosslinked with other copolymers.

The expression "block copolymer" as used herein is defined as a high molecular weight polymer where each monomer forms homopolymer segments and different homopolymer segment types are linked together.

The random copolymer is composed of a primary comonomer and at least one other secondary comonomer. The expression "primary comonomer" as used herein is defined as the comonomer that gives the copolymer chain its basic sieving properties.

The expression "secondary comonomer" as used herein is defined as a comonomer, other than the primary comonomer, that incorporates a desired property into the targeted random copolymer being synthesized.

The term "support" as used herein is defined as any device that functions to contain gel matrices for use in electrophoresis separations and defines a path through which an electrophoretically separated sample migrates.

The term "reactivity" as used herein is defined as the probability that a given monomer is added to a growing copolymer chain in the presence of other types of monomers.

The random copolymers of the claimed invention are sieving components used to separate biomolecules, for example, proteins, nucleic acids, peptides, and the like, by slab gel electrophoresis, capillary electrophoresis, isoelectric focusing, electrophoresis on micromachined channels, or capillary electrophoresis on a chip technology. The capillary electrophoresis can be performed in either coated or uncoated capillaries. The random copolymers are neutral or ionic and has low intrinsic fluorescence.

The random copolymers of the claimed invention are strategically synthesized by selecting specific comonomers to form a targeted linear copolymer. The random copolymers are composed of at least two or more comonomer types. The ratio of comonomers can be continuously adjusted to optimize the properties for electrophoretic separation. The ratio of comonomers may be any ratio that provides the desired properties of the random copolymer. The comonomers must be water soluble. Typically, there is a primary comonomer that gives the random copolymer chain its primary physical, chemical, and sieving properties. Preferably, the primary comonomer is an acrylamide or an acrylamide derivative where it contains between 3–24 carbon atoms, is saturated or unsaturated, and is substituted or unsubstituted. Examples of acrylamide derivatives include, but are not limited to, N,N-dimethacrylamide, N,N-dimethylmethacrylamide, N-ethylmethacrylamide, N-ethylacrylamide, N-methylacrylamide, N-methylmethacrylamide, and methacrylamide. The primary comonomers are available commercially or by simple derivatization of monomer units.

The secondary comonomers are selected for their inherent properties that may be incorporated into the copolymer chains. These inherent properties include, but are not limited to, one or more of hydrophilicity, hydrophobicity, self coating properties, copolymer chain backbone stiffness, stability of copolymer entanglement structure at different temperature and electric fields, resistance to hydrolysis, processivity of copolymer chain extension, gel matrix viscosity, affinity of the copolymer to the surface of a suitable supporting substrate, such as a coating layer on the inner surface or exposed bare surface of a capillary tubing, and chirality. The preferred inherent properties of the secondary comonomers are hydrophilicity, hydrophobicity, viscosity, and self coating properties. The selection of the secondary comonomers and the ratio of secondary comonomers to primary comonomer are based on predetermined desired properties of the targeted random comonomer.

At least one secondary comonomer may be copolymerized with the primary comonomer to form a random copolymer, wherein each comonomer unit is distributed along the copolymer chain in no specific order, and the ratio of the reactivity of the primary comonomer to the secondary comonomers is between about 0.3 to about 2. The reactivity is the probability that a given monomer is added to a growing copolymer chain in the presence of other types of monomers. Formation of the random copolymers is not limited to the copolymerization of one secondary comonomer with the primary comonomer. More than one secondary comonomer may be present in the formation of the random copolymers.

The present invention is further realized by forming a gel matrix that contains a copolymer formed from a first comonomer and at least a second comonomer having a reactivity of about 0.3 to about 2. When multiple monomers are utilized, the ratio of reactivities of all the secondary comonomers is between about 0.3 to about 2. It is presumed that the reactivity is correlated with the chemical structure of the comonomers. Thus, one can choose suitable secondary comonomers based on chemical structure alone.

In another embodiment, the secondary comonomer or comonomers are vinyl monomers, monomers of acrylamide derivatives, monomers of acryloyl derivatives, monomers of acrylic acid derivatives and mixtures thereof. Preferably, the secondary comonomers are vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, and mixtures thereof, each having between 2–24 carbon atoms, is saturated or unsaturated, and is substituted or unsubstituted. More preferably, the secondary comonomers are acrylamide, methacrylamide, N-acryloylmorpholine, N-allylacrylamide, N-allylmethacrylamide, N, benzylacrylamide, N-benzylmethacrylamide, N-(iso-butoxymethyl) acrylamide, N-(iso-butoxymethyl) methacrylamide, N-(tert-butyl)acrylamide, N-tert-butyl)methacrylamide, N-cyclohexylacrylamide, N-cyclohexylmethacrylamide, N,N-diethylacrylamide, N,N-diethylmethacrylamide, N-[2-(N,N-dimethylamino)ethyl]acrylamide, N-[2-(N,N-dimethylamino)ethyl]methacrylamide, N-[3-(N,N-dimethylamino)propyl]acrylamide, N-[3-(N,N-dimethylamino)propyl]methacrylamide, N,N-dimethylacrylamide, N-methylmethacrylamide, N-methylacrylamide, N-ethylacrylamide, N-ethylmethacrylamide, N-phenylacrylamide, N-phenylmethacrylamide, N,N-diphenylacrylamide, N,N-diphenylmethacrylamide, N,N-dodecamethylenebisacrylamide, N-dodecylacrylamide, N-dodecylmethacrylamide, N-(2-hydroxypropyl)acrylamide, N-(2-hydroxypropyl)methacrylamide, N,N-methylenebismethacrylamide, N-methylolacrylamide, N-methylolmethacrylamide, N-propylacrylamide, N-propylmethacrylamide, N-isopropylacrylamide, N-isopropylmethacrylamide, N-butylacrylamide, N-butylmethacrylamide, N-isobutylacrylamide, N-isobutylmethacrylamide, vinyl acetate, vinylacetic acid, vinylbenzyl alcohol, vinylcyclohexane, N-vinyl formamide, 1-vinyl-2-pyrrolidinone, vinyl acetonitrile, vinyl acrylate, vinyl 4-tert-butylbenzoate, N-vinylcaprolactam, vinyl crotonate, vinylcyclopentane, vinyl decanoate, vinyl carbonate, vinyl 2-ethylhexanoate, 1-vinylimidazole, vinyl methacrylate, 2-vinylnaphthalene, 2-vinylpyridine, 4-vinylpyridine, vinyl sulfone, ethylene glycol vinyl ether, 1,6-hexanediol vinyl ether, N-vinylphthalimide, vinyl pivalate, 1-vinyl-2-pyrrolidinone, vinyl trifluoroacetate, and 4,4'-vinylidenebis(N,N-dimethylaniline), or mixtures thereof.

The random copolymers are synthesized by copolymerization of comonomers using methodology well known to those of ordinary skill in the art. The preferred method of copolymer synthesis is free-radical solution polymerization. Any free radical initiator well known to those of ordinary skill in the art may be used, including, but not limited to, peroxy compounds, azoalkanes, photochemical homolysis, biradicals, tin hydrides, alkyl amines, and heat. Preferably, the free radical initiator is a peroxy compound, an azoalkane, or alkylamine.

Typical polymerization initiators known to those of ordinary skill in the art can be used in the present invention. For instance, these initiators may be capable of generating free radicals. Suitable polymerization initiators include both thermal and photoinitiators. Suitable thermal initiators include, but are not limited to, ammonium persulfate/tetramethylethylene diamine, 2,2'-azobis-(2-amidino propane)hydrochloride, potassium persulfate/dimethylaminopropionitrile, 2,2'-azobis(isobutyronitrile), 4,4'-azobis-(4-cyanovaleric acid), and benzoylperoxide. Preferred thermal initiators are ammonium persulfate/tetramethyethylenediaamine and 2,2'-azobisisobutyronitrile ("AIBN"). Suitable photoinitiators include, but are not limited to, isopropylthioxantone, 2-(2'-hydroxy-5'-methylphenyl)benzotriazole, 2,2'-dihydroxy-4-methoxybenzophenone, and riboflavin. When using the combination of persulfate and tertiary amine, the persulfate is preferably added prior to the addition of the non-aqueous medium, since persulfate is much more soluble in water than in non-aqueous dispersing media. More preferably, the free radical initiator is N,N,N',N'-tetramethylethylene-diamine ("TEMED"), or AIBN.

Other methods of synthesizing the copolymers of the present invention are described in Goetzinger, W., et al., Electrophoresis, 1998, 19, 242–249 (inverse emulsion polymerization); and Sassi, A., et al., Electrophoresis, 1996, 17, 1460–1469 (suspension polymerization and precipitation polymerization).

In the present invention, the copolymerization process is done in the absence of crosslinking agents, to form linear, non-crosslinked copolymers. All copolymers are dissolved in the same bulk solution prior to copolymerization and each comonomer unit along the synthesized chain is distributed in a random fashion. There are no well-defined blocks of comonomer units as a result of the random distribution. However, the placement of each comonomer unit along the chain results in a uniform distribution of each comonomer unit. The copolymer is a linear random copolymer having molecular weights of between about 100,000 to 5,000,000 Daltons. Typically, the copolymerization process is done at temperatures between about 0° C. to about 80° C. Preferably, the copolymerization process is done at temperatures between about 5° C. to about 40° C. More preferably, the copolymerization process is done at temperatures between about 15° C. to 30° C.

The copolymerization process is carried out in the presence of an inert atmosphere and in the absence of oxygen, which may be facilitated by freeze-thaw, vacuum degassing, gas purging by bubbling the reaction solution, or other methods known to those of ordinary skill in the art. Typical gases that may be used include, but are not limited to, helium, argon, and nitrogen. Vacuum degassing or helium gas purging are the preferred methods of removing oxygen content. Typically, vacuum degassing was applied for about 30 minutes to 2 hours, and helium gas purging was done for about 1.5 hours to about 3 hours.

The method of preparing the gel matrices for electrophoresis may be done by dispersing pre-polymerized linear random copolymers of this invention in a given volume of aqueous medium, and mixing thoroughly by suitable means, e.g., vortexing, gentle shaking, or mechanical stirring. Typically, the matrix is allowed sit for 3 to 24 hours after mixing to insure complete dissolution of the material. Preferably, the matrix is allowed to sit for 5 to 15 hours, and more preferably 10 to 12 hours. The pre-polymerized linear random copolymers may be formed by polymerizing the comonomers in either aqueous buffer or water using methodology well known to those of ordinary skill in the art, and filtering to yield the isolated product. The pre-polymerized linear random copolymers may also be isolated by extraction methods known to those of ordinary skill in the art, and subsequent removal of the solvent.

In another embodiment, the method of preparing gel matrices for electrophoresis involves controlling chemical, physical and sieving properties by the judicial selection of specific primary and secondary comonomers, and careful control of the comonomer ratios and reaction conditions.

In another embodiment, the method of preparing the gel matrices for electrophoresis involves copolymerization of desired amounts of the comonomers in a aqueous solution having a pH between about 5 to about 11 at a sufficient temperature, pressure and time to yield a gel matrix that is ready for use in electrophoresis separations. When the aqueous solution is water, the pH is preferably between about 5 to about 8. When the aqueous solution is a buffer, the pH is preferably between about 7 to about 9. The buffer solutions of the present invention include aqueous solutions, organic solutions, or mixtures thereof. Selection and incorporation of a suitable buffer is well known to those of ordinary skill in the art and is dependent upon the materials to be separated by the electrophoresis process in which the medium containing the copolymer is employed. Such buffers that may be selected and are commonly used are described, for example, in Andreas Chrambach, "The Practice of Quantitative Gel Electrophoresis," VCH Publishers, Deerfield Beach, Fla., (1985), and U.K. Laemmli, Nature, 227:680, (1970). Preferred buffer systems are tris (hydroxymethyl)aminomethane("Tris")/borate/ethylenediaminetetraacetic acid ("EDTA"), Tris/acetate/EDTA, Tris/phosphate/EDTA, and Tris/glycylglycine/EDTA. Other additives in the buffer may also be present, such as formamide or urea. More preferably, the buffer is a Tris/borate/EDTA, formamide solution or a Tris/borate/EDTA, urea buffer solution. Typically, urea concentrations in these buffer solutions are between about 3 M to about 10 M, Tris concentrations are between about 50 mM to about 150 mM, and EDTA concentrations are between about 0.1 mM to 100 mM. Preferably, the urea concentrations in these buffer solutions are between about 5 M to about 8 M, the Tris concentrations are between about 70 mM to about 120 mM, and the EDTA concentrations are between about 0.5 mM to 20 mM. More preferably, the urea concentrations in these buffer solutions are between about 6 M to about 7 M, the Tris concentrations are between about 80 mM to about 100 mM, and the EDTA concentrations are between about 1 mM to about 5 mM.

The concentration of the random copolymers in the gel matrix is any quantity which provides retention times in electrophoretic separations of the sample molecules such that effective separation on the basis of molecular size and/or charge is achieved. This concentration will vary with respect to the parameters of the separation system, including, for example, the column configuration and length; the effect of other factors influencing the separation, such as charge and electrophoretic mobility; the molecular structure; intrinsic viscosity; the interactive character of the polymer itself; and the range of and differences between the molecular weights of the sample molecules. Typically, the concentration of the random copolymers in the gel matrix is from about 0.01 to about 10.0 weight percent. Preferably, the concentration of the random copolymers in the gel matrix is from about 2 to about 5 weight percent. More preferably, the concentration of the random copolymers in the gel matrix is from about 3 to about 4 weight percent.

The secondary comonomer can be selected to impart viscosity properties into a copolymer chain. In the copolymer, the ratio of secondary comonomer with inherent viscosity properties to primary comonomer is any ratio that results in the desired viscosity of the gel matrix. The control of viscosity is an important property that affects many aspects of gel electrophoresis. For example, high viscosities in gel matrices often make it difficult to fill and flush capillary tubes. An important advantage of the present invention is the flexible optimization of viscosity such that a gel matrix has a low enough viscosity that enables easy filling and flushing of capillary tubes. This allows the user to easily change the gel matrices to suit a particular system or separation. The desired viscosity may also be fine tuned to avoid low viscosities that are susceptible to temperature or electric field gradients when temperature or electric field changes in the system occur. These gradients cause poor resolution and separation performance. Furthermore, low viscosities causes gel matrices in non-horizontal capillaries to flow downwards due to gravitational forces, thereby causing poor separation of biological molecules.

The viscosities of the random copolymer gel matrices were measured by the falling-ball method, one which is well known to those of ordinary skill in the art (R. L. Daugherty, J. B. Franzini, and E. J. Finnermore, "Fluid Mechanics with Engineering Applications," $8^{th}$ edition, McGraw-Hill, Inc., p. 401, 1985). Typically, the viscosities of the gel matrices is between about 10 to about 100,000 Cp, preferably, between about 500 to about 50,000 Cp, and more preferably between about 1500 to about 20,000 Cp.

The secondary comonomer can be selected to impart hydrophilicity into a copolymer chain. In the copolymer, the ratio of secondary comonomer with inherent hydrophilicity to primary comonomer is any ratio that results in the desired hydrophilicity of the gel matrix. One advantage of controlling the hydrophilicity of a gel matrix is to ensure DNA, protein, and peptide solubility, which subsequently facilitates high levels of separation performance, including complete resolution of the components in a sample, reproducibility, and accuracy.

The secondary comonomer can be selected to impart self coating properties into a copolymer chain. In the copolymer, the ratio of secondary comonomer with inherent self coating properties to primary comonomer is any ratio that results in the desired self coating properties of the gel matrix. One advantage of controlling self coating properties is it suppresses electroendoosmotic flow when using uncoated capillaries for electrophoretic separations.

The present invention also relates to a capillary tube filled with an electrophoresis separation medium comprising a gel matrix of at least one random, linear copolymer. The copolymer comprises a primary comonomer and at least one secondary comonomer, wherein the comonomers are randomly distributed along the copolymer chain. The primary comonomer is an acrylamide or an acrylamide derivative that provides the primary physical, chemical, and sieving properties of the gel matrix. The at least one secondary comonomer imparts an inherent physical, chemical, or sieving property to the copolymer chain, and the ratio of reactivity of the at least one secondary to primary comonomer is between about 0.3 to about 2. The primary and secondary comonomers are present in a ratio sufficient to induce desired properties that optimize electrophoresis performance. The desired properties incorporated by the secondary comonomers are hydrophilicity, hydrophobicity, copolymer chain backbone stiffness, stability of copolymer entanglement structure, resistance to hydrolysis, processivity of copolymer chain extension, gel matrix viscosity, affinity of the copolymer to the surface of a supporting substrate, chirality, or a mixture thereof. The gel matrix has a viscosity of between about 1500 to about 20,000 Cp, and the linear random copolymers have molecular weights of between about 100,000 to 5,000,000 Daltons.

This invention also relates to a method of separating biological molecules, for example, proteins, nucleic acids, peptides, and the like, by electrophoretically passing these molecules through a gel matrix containing the random copolymers of the present invention. These steps include placing a gel matrix of random, linear copolymers in a support, adding the mixture of biological molecules to the electrophoretic separation medium at one end of the support, and applying an electric field to the medium having a strength sufficient to facilitate the migration and separation of the biological molecules. The support has two spaced apart regions having a path in which a voltage differential may be applied to cause samples to migrate within the gel matrix. Preferably, the separation of biological molecules is done by using the random copolymers of the present invention in slab gel electrophoresis, capillary electrophoresis, isoelectric focusing, electrophoresis on micromachined channels, or capillary electrophoresis on a chip technology.

Separations were typically carried out using an electric field strength sufficient to facilitate migration and separation of biological molecules. The electric field was generated using a power supply configured to apply a voltage differential at two spaced apart regions of a supported gel matrix. Preferably, the electric field strength is between about 50 V/cm and about 300 V/cm. More preferably, the electric field strength is between about 100 V/cm and about 200 V/cm. Most preferably, the electric field strength is between about 125 V/cm and about 175 V/cm.

In one embodiment, the support is a mold for slab gels. The mold has a cavity to accommodate the gel matrix of the present invention in slab form. This embodiment encompasses the use of all commonly used molds which hold electrophoresis media for use in slab gel electrophoresis.

In another embodiment, the support is a capillary tube. Any capillary having sufficient length, inner diameter, and outer diameter to facilitate electrophoretic separations of biological molecules may be used. The capillaries may be composed of any inert material, and preferably, capillaries are fused-silica capillaries. Typical capillaries are those having internal diameters of less than about 200 $\mu$m, outer diameters of between about 100 and 500 $\mu$m, and lengths of between about 10 cm to 150 cm. Preferably, the capillaries have internal diameters of between about 25 $\mu$m and 150 $\mu$m, outer diameters of between about 200 and 400 $\mu$m, and lengths of between about 30 cm to 110 cm. More preferably, the capillaries have internal diameters of between about 50 μm and 100 μm, outer diameters of between about 250 and 365 μm, and lengths of between about 55 cm to 80 cm.

In another embodiment, the support is a micromachined channel. In particular, this support comprises etched grooves on an inert surface, such as silica or silicon, and the grooves contain the gel matrices of the present invention. Furthermore, the micromachined channel contains a path for the electrophoretic separation biological molecules.

An advantage of the present invention is the flexible optimization of the chemical, physical, and sieving properties by the careful selection of the comonomers and ratios of comonomers. Depending on the needs of a particular separation, a gel matrix may be prepared using random linear copolymers of the present invention that have desired properties to enable effective separations of biological molecules. For example, separations using uncoated capillaries inevitably lead to electroendoosmosis, where the gel matrix migrates within the capillary tube. As a consequence, separation of biological molecules is not efficient, accurate or reproducible. The use of a gel matrix containing random copolymers with self coating properties allows the gel matrix to adsorb onto the silica of the capillary tube, thereby suppressing electroendoosmotic flow.

The invention is further defined by reference to the following examples, describing in detail the preparation of the compound and the compositions of the present invention, as well as their utility. It will be apparent to those of ordinary skill in the art that many modifications, both to materials and methods, may be practiced without departing from the purpose and interest of this invention.

EXAMPLES

Example 1

Preparation of 5.0% DMA+0.5% AA Gel Matrix

1×TBE, 6 M buffer was prepared by dissolving 89 millimoles (mM) of tris(hydroxymethyl)aminomethane(Tris), 2 mM ethylenediaminetetraacetic acid (EDTA), and 6 moles of urea to 1 L of deionized water. 50 mL 1×TBE, 6 M urea buffer was transferred to a 250 mL PYREX bottle. 5.0 g dimethyl acrylamide (DMA) and 0.5 g sodium acrylate (NaAA) were weighed and added to the buffer solution. The final volume was brought up to 100 mL with additional buffer solution. The solution was degassed for 30 minutes in a desiccator chamber with its outlet connected to a diaphragm vacuum pump. After degassing, 25 μL of N,N,N',N'-tetramethylethylenediamine(TEMED) and 25 μL of 40% (v/v) ammonium persulfate (ASP) were added to the solution. The bottle was capped, and the polymerization was carried out at room temperature for 12 hours.

Example 2

Preparation of 3.5% AAm and 1.5% DMA Gel Matrix

1×TBE, 7 M buffer was prepared by dissolving 89 mM of Tris, 2 mM EDTA, and 7 moles of urea to 1 L of deionized water. 19 mL of 1×TBE, 7 M urea buffer was transferred to a 20 mL scintillation vial. 0.30 g of DMA and 0.70 g acrylamide (AAm) were weighed and added to the buffer solution. Helium was bubbled into the solution at 10 psi for 1 hour. After degassing, 25 μL of TEMED and 25 μL of 40% (v/v) ASP were added to the solution. The bottle was capped, and the polymerization was carried out at room temperature for 12 hours.

Example 3

Preparation of 2.5% AAm and 2.5% DMA Gel Matrix

1×TBE, 7 M buffer was prepared by dissolving 89 mM of Tris, 2 mM EDTA, and 7 moles of urea to 1 L of deionized water. 19 mL of 1×TBE, 7 M urea buffer was transferred to a 20 mL scintillation vial. 0.50 g of DMA and 0.50 g AAm were weighed and added to the buffer solution. Helium was bubbled into the solution at 10 psi for 1 hour. After degassing, 25 μL of TEMED and 25 μL of 40% (v/v) ASP were added to the solution. The bottle was capped, and the polymerization was carried out at room temperature for 12 hours.

Example 4

Preparation of 4.5% AAm and 0.5% DMA Gel Matrix

1×TBE, 7 M buffer was prepared by dissolving 89 mM of Tris, 2 mM EDTA, and 7 moles of urea to 1 L of deionized water. 19 mL of 1×TBE, 7 M urea buffer was transferred to a 20 mL scintillation vial. 0.90 g of AAm and 0.10 g DMA were weighed and added to the buffer solution. Helium was bubbled into the solution at 10 psi for 1 hour. After degassing, 25 μL of TEMED and 25 μL of 40% (v/v) ASP were added to the solution. The bottle was capped, and the polymerization was carried out at room temperature for 12 hours.

Example 5

Preparation of 3.0% AAm+1.0% DMA+0.06% AA Gel Matrix

1×TBE, 7 M buffer was prepared by dissolving 89 mM of Tris, 2 mM EDTA, and 7 moles of urea to 1 L of deionized water. 50 mL of 1×TBE, 7 M urea buffer was transferred to a 250 mL PYREX bottle. 3.0 g of AAm, 1.0 g DMA and 0.06 g NaAA were weighed and added to the buffer solution. The final volume was brought up to 100 mL with additional buffer. Helium was bubbled into the solution at 10 psi for 1 hour. After degassing, 25 μL of TEMED and 25 μL of 40% (v/v) ASP were added to the solution. The bottle was capped, and the polymerization was carried out at room temperature for 12 hours.

Example 6

Preparation of 3.0% AAm+1.0% DMA+0.06% AA Gel Matrix

1×TBE, 3.5 M buffer was prepared by dissolving 89 mM of Tris, 2 mM EDTA, and 7 moles of urea to 1 L of deionized water. 50 mL of 1×Tris, 3.5 M urea buffer was transferred to a 250 mL PYREX bottle. 3.0 g of AAm, 1.0 g DMA and 0.06 g NaAA were weighed and added to the buffer solution. The final volume was brought up to 100 mL with additional buffer. Helium was bubbled into the solution at 10 psi for 1 hour. After degassing, 25 μL of TEMED and 25 μL of 40% (v/v) ASP were added to the solution. The bottle was capped, and the polymerization was carried out at room temperature for 12 hours.

Example 7

Figure 1:
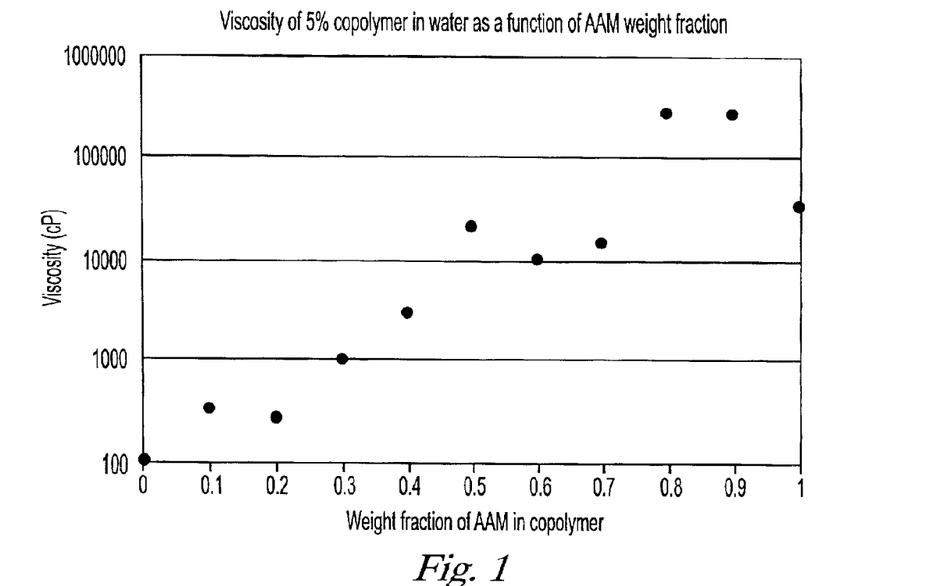
FIG. 1 illustrates the viscosity of acrylamide-co-dimethylacrylamide copolymers as a function of the weight fraction of acrylamide (AAm).

Viscosity Measurement Gel Matrices Containing 5% of the Random Copolymer, Poly(acrylamide)$_x$-co-(N,N-dimethylacrylamide)$_{1-x}$ in Water FIG. 1 shows the measured viscosities of gel matrices containing 5% of the random copolymer, poly(acrylamide)

$_x$-co-(N,N-dimethylacrylamide)$_{1-x}$ in water as a function of weight fraction of acrylamide ("AAM"). The viscosity measurement was done by using the falling-ball method. The weight fractions of AAM to the total weight of monomers, AAM, and N,N-dimethylacrylamide ("DMA") were varied in the series of copolymers such that the total monomer concentration stays at a constant 5%. Viscosity measurements were taken at a temperature of 22° C. The viscosity of the polymer solution can be tuned in the range of more than three orders of magnitude. The plot in FIG. 1 clearly shows that the effect of increasing the ratio of AAM causes an increase in the viscosity of the gel.

Example 8

Hydrophilicity Measurements

Figure 2:
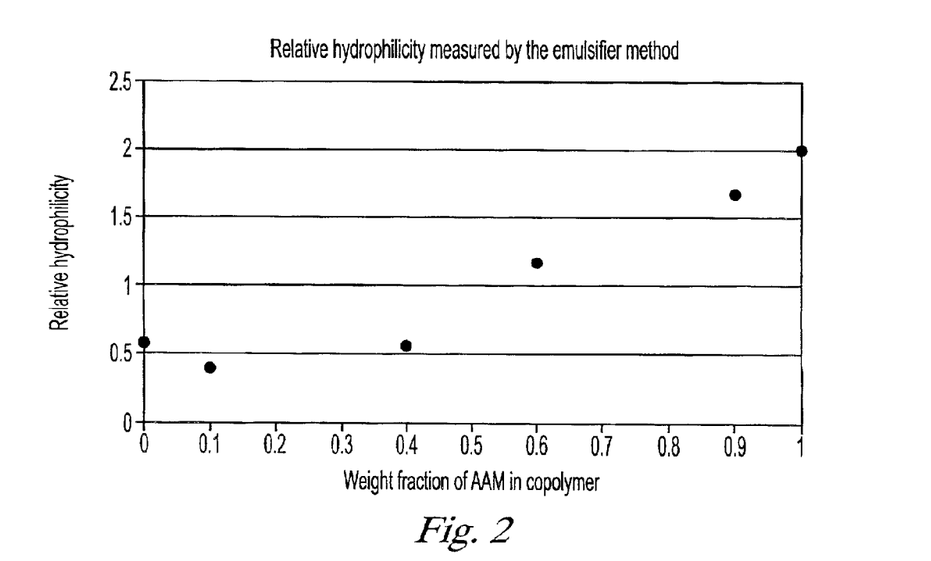
FIG. 2 illustrates the relative hydrophilicity of acrylamide-co-dimethylacrylamide copolymers as a function of the weight fraction of acrylamide (AAm).

Hydrophilicities of monomers have been measured with the partition coefficients between water and n-octanol after vigorous stirring. Upon equilibration, the monomer quantity of the aqueous phase was weighed after the water was evaporated. The partition coefficients of the monomers, AAM, and DMA in aqueous phase are 0.80 and 0.50, respectively. As shown in FIG. 2, the DMA polymer (weight fraction of AAM=0, relative hydrophilicity=0.5 a.u.) has a hydrophilicity less than that of AAM polymer (weight fraction of AAM=1, relative hydrophilicity=2 a.u.). The hydrophilicities were studied by the same method. The gel containing 5% poly(acrylamide)$_x$-co-(N,N-dimethylacrylamide)$_{1-x}$, in which different ratios of AAM and DMA were used, was synthesized in water. The resulting copolymer was diluted to 1%, and then an appropriate amount of n-octanol was added to make a 3:7 n-octanol/water ratio by volume. The resulting copolymer solution was vigorously stirred at 600 rpm for two hours. The solution was then allowed to sit at ambient conditions for another two hours to separate the organic phase from the aqueous phase, and the organic phase was collected. A reference sample of water and n-octanol with the same volume, in the absence of polymer, were treated with the same procedures as the 1% copolymer in 3:7 n-octanol/water. The volume loss of n-octanol, defined as the volume difference between the reference sample and copolymer samples, shows the volume of n-octanol that has been taken up by the copolymers. The reduced volume loss of n-octanol indicates that polymer is more hydrophilic. FIG. 2 shows a plot of the ratio of copolymer weight (g) to the n-octanol volume loss (mL), which represents the relative hydrophilicity of the copolymers. It is clear from this plot that an increase in the weight fraction of AAM increases the hydrophilicity of the gel.

Example 9

The Separation of PGEM/U DNA Sequencing Samples Using (3.5% DMA+1.5% AAm) Copolymer Gel in Uncoated and Coated μFC Capillaries PGEM/U DNA sequencing samples were separated using (3.5% DMA+1.5% AAm) Copolymer Gel in Uncoated and Coated μFC Capillaries.

A. Preparation of Electrophoretic Gels

The (3.5% DMA+1.5% AAm) Copolymer Gel was prepared by the following procedure:

19 mL 1×TBE, 7 M urea buffer was transferred to a 250 mL PYREX bottle. 0.7 g dimethyl acrylamide (DMA) and 0.3 g acrylamide (AAm) were weighed and added to the buffer solution. The solution was bubbled with helium for 60 minutes at 10 psi. After purging, 5 μL of N,N,N',N'-tetramethylethylenediamine(TEMED) and 5 μL of 40% (v/v) ammonium persulfate (ASP) were added to the solution. The bottle was capped, and the polymerization was carried out at room temperature for 12 hours.

B. Capillary Electrophoresis Apparatus

Figure 3:
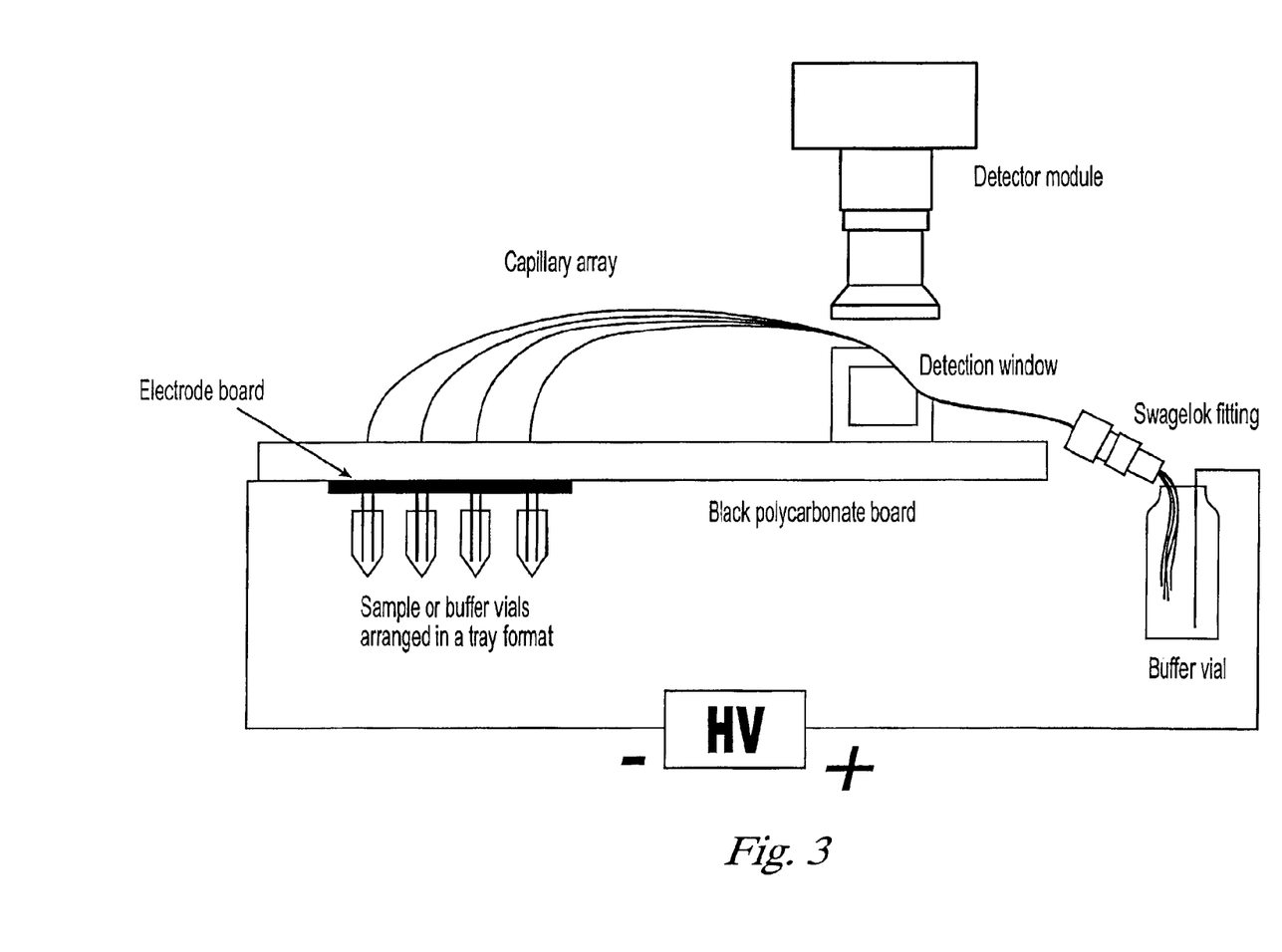
FIG. 3 is the schematic drawing of a capillary electrophoresis apparatus with laser induced fluorescence detection.

Separations of the DNA samples were carried out using a capillary electrophoresis apparatus equipped with a laser induced fluorescence detector. FIG. 3 is a schematic drawing of the capillary electrophoresis apparatus, showing a polycarbonate board that provides the mounting base for the other components, including the capillary array, detection window mount, high pressure fitting, and electrode boards holding individual electrodes for each capillary.

The fused-silica capillaries are typically 55–80 cm in length, with a 75 μm inner diameter and 200–365 μm outer diameter. The capillary array consisting of 2–96 capillaries is arranged in a flat ribbon format. At a distance of about 20 cm from one end of the capillary array, the polyimide coating of the capillaries is stripped off by hot wire heating to create a 1.5 to 2 cm wide translucent window for laser excitation and fluorescence light collection.

The detector module is mounted above the translucent window to simultaneously monitor all the capillaries. An incoming laser beam perpendicular to the drawing plane intersects with all the capillaries and excites fluorescence from the bypassing fluorophore samples migrating within the capillaries.

Gel filling of the capillaries is done by connecting the capillaries to a gel filling tube, and applying a nitrogen or helium gas pressure of between 100 to 500 psi for 5 to 60 minutes, depending on the gel viscosity. For capillary flushing, the end of the capillaries are connected to an HPLC pump and are typically flushed at 500 to 1000 psi with an aqueous 0.2% poly(vinylpyrrolidone) solution for 30 to 60 minutes after each run.

An array of 4 to 16 capillaries were used. Uncoated capillaries were purchased from Polymicro Technologies, and coated μFC capillaries were purchased from J&W Scientific.

C. DNA Samples

The DNA sequencing samples were PGEM/U samples prepared with the BIGDYE terminator sequencing kit (Perkin-Elmer, Applied Biosystems Division, Foster City, Calif.). The samples were purified with spin columns and dried under vacuum. Prior to electrophoresis, the sample was resuspended in 5 μL of formamide and 25 mM EDTA mixed denaturing solution. The sample was heated at 95° C. for 2 minutes and chilled on ice prior to electrokinetic injection into the capillary. Typically, the sample was injected in an environment having a 75 V/cm electric field with a duration of 40–60 seconds. All separations were performed using a 150 V/cm electric field.

Figure 4A:
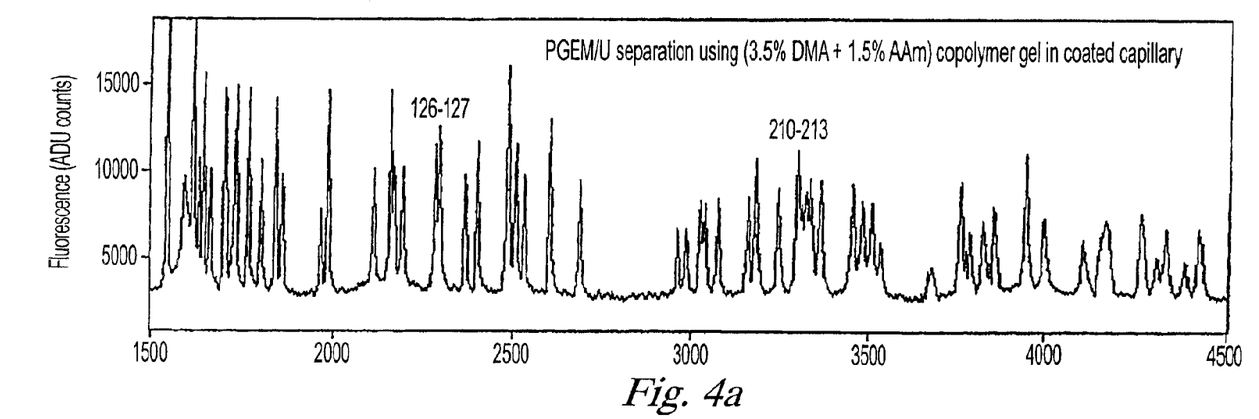
FIG. 4 illustrates the #1 color electrophorogram of the electrophoretic separation of PGEM/U DNA samples. The #1 color consists mostly of fluorescence from the G fragments in the DNA sequencing samples.
Figure 4B:
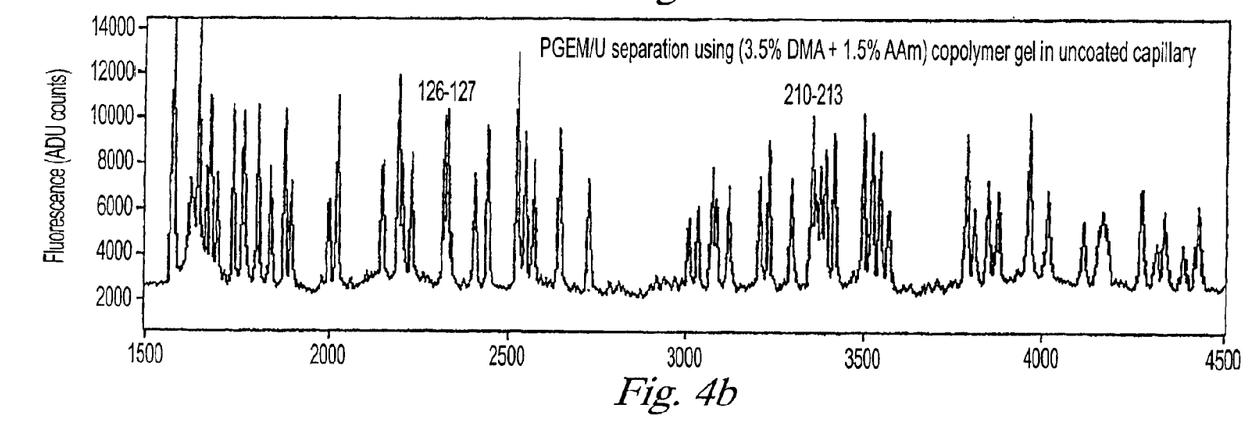

D. PGEM/U Separations Using (3.5% DMA+1.5% AAm) Copolymer Gel in Uncoated and Coated μFC Capillaries Uncoated and coated capillaries were filled with (3.5% DMA+1.5% AAm) Copolymer Gel according to the methods described above. FIG. 4A shows the separation of PGEM/U in the coated capillary, and FIG. 4B shows the separation of PGEM/U in the uncoated capillary. The μFC coating of the coated capillaries function to suppress electroendoosmotic flow. The retention times of the 210–213 peaks in both separations are nearly identical (ca. 3300 frame numbers in FIG. 4A, and ca. 3360 frame numbers in FIG. 4B). This suggests that the copolymer gel effectively suppresses electroendoosmotic flow by adsorbing onto the silica surface of the uncoated capillary tube.

What is claimed is:

1. A capillary tube, free of a covalent coating and filled with an electrophoresis separation medium comprising gel matrix of at least one random, linear copolymer comprising a primary comonomer and at least one secondary comonomer, wherein the comonomers are randomly distributed along the copolymer chain; wherein the primary comonomer is acrylamide; and the at least one secondary comonomer comprises one from the group consisting of vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, or mixtures thereof, each having between 2–24 carbon atoms.

2. The capillary tube of claim 1, wherein the primary comonomer is acrylamide and the at least one secondary comonomer is dimethylacrylamide.

3. The capillary tube of claim 1, wherein said at least one secondary comonomer imparts one or more of hydrophilicity, hydrophobicity, copolymer chain backbone stiffness, self coating properties, stability of copolymer entanglement structure, resistance to hydrolysis, processivity of copolymer chain extension, gel matrix viscosity, affinity of the copolymer to the surface of a supporting substrate, or chirality.

4. The capillary tube of claim 1, wherein said at least one secondary comonomer imparts self coating properties.

5. The capillary tube of claim 1, wherein the capillary tube, is uncoated.

6. The capillary tube of claim 1, further comprising poly(vinylpyrrolidone).

7. The capillary tube of claim 1, wherein the capillary tube is a capillary tube of an array of capillary tubes, each capillary tube of the array of capillary tubes comprising the copolymer.

8. The array of capillary tubes of claim 7, wherein the array consists of 16–96 capillary tubes.

9. A method of separating a mixture of biological molecules within an electrophoretic separation medium comprising:

a) introducing into a capillary tube, free of a covalent coating and a gel matrix of at least one random, linear copolymer comprising a primary comonomer and at least one secondary comonomer, wherein the comonomers are randomly distributed along the copolymer chain; wherein the primary comonomer is acrylamide; and the at least one secondary comonomer comprises one from the group consisting of vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, or mixtures thereof, each having between 2–24 carbon atoms;

b) adding the mixture of biological molecules to the electrophoretic separation medium at one end of the capillary tube; and c) applying an electric field to the medium in an amount sufficient to facilitate the migration and separation of the biological molecules.

10. The method according to claim 9, wherein the primary comonomer is acrylamide and the at least one secondary comonomer is dimethylacrylamide.

11. A capillary tube, free of a covalent coating and filled with an electrophoresis separation medium comprising a gel matrix of at least one random, linear copolymer comprising a primary comonomer and at least one secondary comonomer, wherein the comonomers are randomly distributed along the copolymer chain; and wherein the primary comonomer is one from the group consisting of acrylamide, N-methylacrylamide, and N-ethylacrylamide; and the at least one secondary comonomer is dimethylacrylamide.

12. The capillary tube of claim 11, further comprising poly(vinylpyrrolidone).

13. A capillary tube, free of a covalent coating and filled with an electrophoresis separation medium comprising a gel matrix of at least one random, linear copolymer comprising a primary comonomer and at least one secondary comonomer, wherein the comonomers are randomly distributed along the copolymer chain; and wherein the primary comonomer is one from the group consisting of acrylamide and acrylamide derivatives other than dimethylacrylamide; and the at least one secondary comonomer is dimethylacrylamide.

14. The capillary tube of claim 13, further comprising poly(vinylpyrrolidone).

15. An electrophoresis method, comprising:

filling a capillary tube, the capillary tube being free of a covalent coating, with a first amount of copolymer, the copolymer being a linear copolymer comprising a primary comonomer and at least one secondary comonomer, wherein the comonomers are randomly distributed along the copolymer chain; wherein the primary comonomer is acrylamide; and the at least one secondary comonomer comprises one from the group consisting of vinyl monomers, monomers of acrylamide derivatives, monomers of acryloyl derivatives, monomers of acrylic acid derivatives, monomers of polyoxides, monomers of polysilanes, monomers of polyethers, monomers of derivatized polyethylene glycols, monomers of cellulose compounds, or mixtures thereof, each having between 2–24 carbon atoms;

subjecting a first plurality of biological molecules to electrophoresis within the first amount of copolymer in the capillary tube;

flushing the copolymer from the capillary tube and filling the capillary tube with a second amount of the copolymer; and subjecting a second plurality of biological molecules to electrophoresis within the second amount of copolymer in the capillary tube.

16. The method of claim 15, wherein:

the step of filling a capillary tube, the capillary tube being free of a covalent coating, with a first amount of the copolymer comprises filing each capillary tube of a plurality of capillary tubes with the copolymer;

the step of subjecting a first plurality of biological molecules to electrophoresis within the capillary tube comprises subjecting a respective first plurality of biological molecules to electrophoresis within each capillary tube;

the step of flushing the copolymer from the capillary tube and filling the capillary tube with a second amount of the copolymer comprises flushing the copolymer from each of the plurality of capillary tubes and filling each capillary tube of the plurality of capillary tubes with a second amount of the copolymer; and the step of subjecting a second plurality of biological molecules to electrophoresis within the capillary tube comprises subjecting a respective second plurality of biological molecules to electrophoresis within each capillary tube of the plurality of capillary tubes.

17. The method of claim 16, wherein the primary comonomer is acrylamide and the at least one secondary comonomer is dimethylacrylamide.

18. The method of claim 16, further comprising introducing poly(vinylpyrrolidone) into each of the capillary tubes intermediate the steps of subjecting respective first plurality of biological molecules to electrophoresis and the respective second plurality of biological molecules to electrophoresis.

19. The method of claim 15, further comprising introducing poly(vinylpyrrolidone) into the capillary tube intermediate the steps of subjecting the first plurality of biological molecules to electrophoresis and the second plurality of biological molecules to electrophoresis.

20. The method of claim 15, wherein the primary comonomer is acrylamide and the at least one secondary comonomer is dimethylacrylamide.

21. The method of claim 15, wherein the step of filling the capillary tube with the first amount of copolymer comprises contacting an uncoated inner surface of the capillary tube with the copolymer.

22. The method of claim 15, comprising subjecting the first plurality of biological molecules to electrophoresis without polymerizing the copolymer intermediate the steps of filling the capillary tube with the first amount of copolymer and subjecting the first plurality of biological molecules to electrophoresis.

* * * * *